(12) United States Patent
Harthun et al.

(10) Patent No.: US 6,462,224 B2
(45) Date of Patent: Oct. 8, 2002

(54) PROCESS FOR THE PREPARATION OF 1,1-CYCLOPROPANEDICARBOXYLIC DIESTERS

(75) Inventors: Andreas Harthun, Niederkassel (DE); Manfred Neumann, Marl (DE); Christoph Theis, Niederkassel (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/739,207

(22) Filed: Dec. 19, 2000

(65) Prior Publication Data

US 2001/0007040 A1 Jul. 5, 2001

(30) Foreign Application Priority Data

Dec. 24, 1999 (DE) .......................... 199 63 115

(51) Int. Cl.[7] .......................... C07C 69/74; C07C 67/30
(52) U.S. Cl. .................. 560/124; 560/127; 560/203
(58) Field of Search ................. 560/124, 203, 560/127

(56) References Cited

U.S. PATENT DOCUMENTS 5,510,509 A * 4/1996 Klaus-Dieter Steffen ... 560/124
6,262,298 B1 * 7/2001 Metz et al. ................. 560/203

FOREIGN PATENT DOCUMENTS

| JP | 06-234705 | * | 8/1994 | |
| JP | 6-234705 | | 8/1994 | |
| JP | 11-180899 | * | 7/1999 | ........... C07B/37/04 |

OTHER PUBLICATIONS

Akira Hirao et al, "Additive Effect of Poly(ethylene oxide), 1. Acceleration Effect of Poly(ethylene oxide) in several Nucleophilic Reactions", Makromol. Chem., vol. 179 (1978), pp. 915–925.*
Aldrich Catalog Handbook of Fine Chemicals 1998–1999, (1988), p. 570.*

* cited by examiner

Primary Examiner—Alan L. Rotman
Assistant Examiner—Hector Reyes
(74) Attorney, Agent, or Firm—Oblon, Spivak, McClelland, Maier & Neustadt, P.C.

(57) ABSTRACT

1,1-cyclopropanedicarboxylic diesters are prepared from malonic diesters, 1,2-dihaloethane and alkali metal carbonate in the presence of a mixture of available or in situ-produced phase transfer catalyst and polyalkylene glycol or derivatives thereof which are capped at one or both ends, in particular those with ether end groups, where the molar ratio of malonic diester: 1,2-dihaloethane: alkali metal carbonate is 1:(1 to 7):(1 to 1.4).

30 Claims, No Drawings

PROCESS FOR THE PREPARATION OF 1,1-CYCLOPROPANEDICARBOXYLIC DIESTERS

BACKGROUND OF THE INVENTION

1. Field of the Invention

The invention relates to a process for the preparation of 1,1-cyclopropanedicarboxylic diesters from malonic diesters, 1,2-dihaloethane and alkali metal carbonate in the presence of a mixture of a phase transfer catalyst and polyalkylene glycol or a capped derivative thereof.

2. Discussion of the Background

A solvent-free process for the cycloalkylation of malonic dialkyl esters, in which a 2-to 5-fold, most preferably 2.2- to 4-fold, molar excess of sodium carbonate or potassium carbonate is used, is described by Katsuro et al. in Japanese patent JP 06 234 705.

A large carbonate excess of this type results in a high salt loading, which prevents industrial realization of the process because of cost and ecological aspects.

Furthermore, water is added to the reaction and water which forms during the reaction is not removed. Accordingly, the water present in the reaction mixture causes partial hydrolysis of the used malonic ester, thus reducing the yield of the target product.

In the above process a quarternary alkylammonium halide is initially introduced at room temperature.

However, experimental results show that this practice leads to partial deactivation of the phase transfer catalyst, and accordingly a large amount of the costly phase transfer catalyst is required. For example, Katsuro et al. used 30 mol % of the phase transfer catalyst tetrabutylammonium bromide (TBAB), based on the malonic diester.

Furthermore, the target product is worked up and isolated via phase separation with subsequent extraction of the aqueous phase which is economically not very attractive. Work-up of this type results in a 1,2-dichloroethane-contaminated waste water stream, the disposal of which is problematical.

SUMMARY OF THE INVENTION

An object of the present invention was therefore to provide a process which does not have the disadvantages as described above.

This and other objects are achieved according to the invention, the first embodiment of which includes a process for the preparation of 1,1-cyclopropanedicarboxylic diesters, comprising:

a) reacting malonic diester, 1,2-dihaloethane and alkali metal carbonate in the presence of available or in-situ-produced phase transfer catalyst and polyalkylene glycol or at least one derivative of polyalkylene glycol which is capped at one or both ends;

wherein a molar ratio of malonic diester: 1,2-dihaloethane: alkali metal carbonate is 1:(1 to 7):(1 to 1.4);

wherein a reaction temperature is $\geq 70°$ C.;

b) azeotropically distilling off water produced during the reaction with 1,2-dihaloethane;

c) separating off the reaction salt by a mechanical separation operation;

d) distilling off an excess of 1,2-dihaloethane; and e) fractionally distilling off said 1,1-cyclopropanedicarboxylic diester;

wherein said reacting proceeds according to the schematic reaction equation

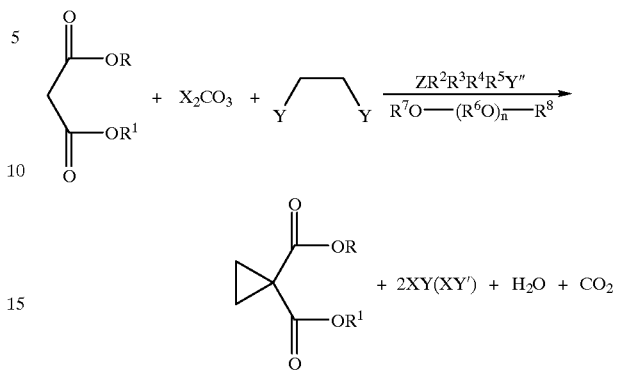

wherein R and $R^1$ independently are an unbranched or branched alkyl group having from 1 to 6 carbon atoms;

Z is nitrogen or phosphorus; and $R^2$, $R^3$, $R^4$ and $R^5$ independently are an unbranched or branched alkyl group having from 1 to 16 carbon atoms, an aryl, alkylaryl or arylalkyl radical having from 6 to 12 carbon atoms or a 1,2-dihaloethyl group;

n is an integer or a fraction from 1 to 30;

$R^6$ is an ethylene radical, a propylene radical, or a mixed compound with ethylene and propylene radicals, and $R^7$ and $R^8$ independently are a hydrogen radical, an unbranched or branched alkyl group having from 1 to 6 carbon atoms or an acyl group having from 2 to 7 carbon atoms;

Y and Y' independently are chlorine, bromine or iodine;

Y" is chloride, bromide, iodide or hydrogen sulfate; and

X is Na or K.

Another embodiment of the invention includes a 1,1-cyclopropanedicarboxylic diester prepared by the above process.

DETAILED DESCRIPTION OF THE INVENTION

We have now found that the addition of a mixture of phase transfer catalyst leads to significantly improved space-time yields during the synthesis of 1,1-cyclopropanedicarboxylic diesters. Preferred phase transfer catalysts are quaternary ammonium halide, polyalkylene glycol or derivatives thereof which are capped at one or both ends, in particular those with ether end groups.

The invention therefore provides a process for the preparation of 1,1-cyclopropanedicarboxylic diesters according to the schematic reaction equation

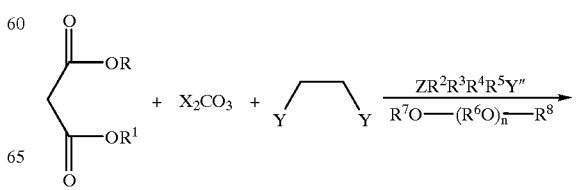

-continued

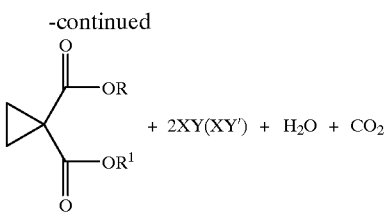

$+ 2XY(XY') + H_2O + CO_2$ which comprises
a) allowing malonic diester, 1,2-dihaloethane and alkali metal carbonate to react in the presence of available or in-situ-produced phase transfer catalyst and polyalkylene glycol or derivatives thereof which are capped at one or both ends, in particular those with ether end groups, where the molar ratio of malonic diester: 1,2-dihaloethane: alkali metal carbonate is 1:(1 to 7):(1 to 1.4), preferably 1:(2.5 to 3.8):(1.1 to 1.4),
b) carrying out the reaction essentially at a reaction temperature of $\geq 70°$ C. on account of the quantitative ratios,
c) distilling off the water of reaction azeotropically with the 1,2-dihaloethane,
d) separating off the reaction salt by means of a mechanical separation operation,
e) distilling off the excess 1,2-dihaloethane, and
f) fractionally distilling off the 1,1-cyclopropanedicarboxylic diester.

R and $R^1$ independently of one another are each an unbranched or branched alkyl group having from 1 to 6 carbon atoms, preferably from 1 to 4 carbon atoms, in particular the methyl, ethyl, n-propyl or n-butyl group. Z is nitrogen or phosphorus as the central atom of the phase transfer catalyst.

$R^2$, $R^3$, $R^4$ and $R^5$ independently of one another are each an unbranched or branched alkyl group having from 1 to 16 carbon atoms, an aryl or alkylaryl radical having from 6 to 12 carbon atoms, preferably the phenyl radical, an aralkyl radical having from 6 to 12 carbon atoms, preferably the benzyl radical, or 1,2-dihaloethane used. In a preferred embodiment, $R^2$, $R^3$, $R^4$ and $R^5$ are identical and are each a butyl group.

$R^6$ is an ethylene or propylene radical, mixed compounds with ethylene and propylene radicals also being included.

$R^7$ and $R^8$ independently of one another are a hydrogen radical, an unbranched or branched alkyl group having from 1 to 6 carbon atoms, preferably a methyl or ethyl group, or an unbranched or branched acyl group having from 2 to 7 carbon atoms.

n is a mean number from 1 to 30, preferably from 2 to 20, and can also be a fraction. n is preferably chosen such that the polyalkylene or polyalkylene glycol derivative is liquid at room temperature.

Y and Y' independently of one another are chlorine, bromine or iodine,

Y" is chloride, bromide, iodide or hydrogen sulfate, and X is Na or K.

Preferred malonic diesters are dimethyl malonate (DMM) or diethyl malonate (DEM). It is also possible to use mixed esters, such as methylethyl malonate, or mixtures of the esters.

The 1,2-dihaloethane is preferably 1,2-dichloroethane (EDC). It is also possible to use mixed 1,2-dihaloethanes with different halogen atoms such as chloride, bromide or iodide.

Preferred alkali metal carbonates are sodium carbonate, potassium carbonate, or mixtures of the two carbonates. Preference is given to using potassium carbonate. The potassium carbonate preferably has a fines content of 85% <0.1 mm and 70% <0.05 mm.

Tetrasubstituted ammonium or phosphonium compounds (quaternary salts) can be used as phase transfer catalysts. The radicals on the nitrogen or phosphorus atom can in principle be different, but are preferably identical. The anion is preferably a halogen ion such as chloride, bromide or iodide. Preferred are tetraalkylammonium salts, more preferred are tetrabutylammonium halide (tetrabutylammonium bromide, TBAB), benzyltrimethylammonium salts or tetrabutylphosphonium salts.

The phase transfer catalyst can also be generated in situ from, for example, trialkylamine and 1,2-dihaloethane.

The polyalkylene glycol used is preferably polyethylene glycol. The same is true for the derivatives which are capped at one or both ends, in particular those with ether end groups, the end groups preferably being methyl or ethyl groups.

The mixing of the starting compounds is not very critical. All of the reactants can be introduced initially and then the mixture can be heated to boiling temperature. It has proven to be overall advantageous to add some of the components once the mixture is at the boil. Thus, in preferred process variants, the phase transfer catalyst and/or the malonic diester is/are metered in at the boil.

The salt can be separated off by means of customary mechanical separation processes, such as decantation, centrifugation or filtration. Filtration is preferred, at least on a laboratory scale.

The above-mentioned procedure for the synthesis of the cyclopropane compounds permits a surprising way of reducing the alkali metal carbonate excess, based on the used malonic diester, to merely 0 to 40%, instead of an alkali metal carbonate excess of from 100 to 400%, as reported by Katsuro et al.

Moreover, it is entirely surprising that even 1 to 20%, preferably from 1 to 15%, more preferably from 1 to 10% and most preferably from 1 to 5% of polyalkylene glycol or derivatives thereof which are capped at one or both ends, in particular those with ether end groups, based on the malonic diester, are sufficient to enable the catalyst content to be reduced to <0.5 mol %. It is preferred to reduce the catalyst content to <0.3 mol %, and even more preferred to <0.1 mol %. The polyalkylene glycols or derivatives thereof are preferably liquid at room temperature and preferably have mean molar masses of from 100 to 800 g/mol. The mean molar mass includes all values therebetween, especially including 200, 300, 400, 500, 600 and 700 g/mol. Moreover, it is also possible to use polyalkylene glycols or derivatives thereof which are viscous or solid at room temperature.

The amount of 1,2-dihaloethane can be reduced to almost ⅓, e.g. from 8.375 mol to 3.16 mol based on 1 mol of malonic ester without a problematical increase in the viscosity of the reaction mixture arising. As a minimum, 1 mol of 1,2-dihaloethane, based on malonic diester, must be used. The amount of 1,2-dihaloethane includes all values therebetween, especially including 1.5, 2.0, 2.5, 3.0, 3.5, 4.0, 4.5, 5.0, 5.5, 6.0, 6.5, 7.0, 7.5 and 8.0 mol based on 1 mol of malonic ester.

Despite the considerable reduction in the excess of the alkali metal carbonate and the considerable reduction in the amount of phase transfer catalyst, a shortening in the reaction time compared with the processes known from the literature is realized, without losses in yield.

The process according to the invention is preferably carried out with recycling of the substance streams produced, with the exception of the desired target product.

Particular advantages of the process are:
a) The addition of the preferably used quaternary alkylammonium halide can also be replaced by the use of a trialkylamine (e.g. triethylamine), i.e. the phase transfer catalyst is produced in situ.
b) The target product can be separated off directly from the reaction salt by means of filtration and be obtained directly, following the distillative removal of 1,2-dihaloethane, by means of distillation.
c) The catalyst-containing distillation residue of the product distillation still has catalytic activity and can be reused for subsequent reactions.

The 1,1-cyclopropanedicarboxylic diesters are intermediates which can be used diversely, inter alia for the preparation of pharmaceuticals and agrochemicals.

Having generally described this invention, a further understanding can be obtained by reference to certain specific examples which are provided herein for purposes of illustration only, and are not intended to be limiting unless otherwise specified.

EXAMPLES

Comparative Example 1 (in accordance with JP 06 234 705, Katsuro et al.)

A reaction vessel was charged with 105.7 g of dimethyl malonate (0.8 mol), 663.0 g of 1,2-dichloroethane (6.7 mol), 279.9 g of potassium carbonate (2 mol) and 77.4 g of tetrabutylammonium bromide (0.24 mol), and the mixture was stirred under reflux at 82° C. for 7 hours. When the reaction was complete, the mixture was cooled to room temperature and taken up in 600 ml of water. Phase separation was carried out and the water phase was extracted with 2×100 ml of 1,2-dichloroethane. The combined organic phases were distilled, and the distillate was worked up again by distillation at 95° C. and 2600 Pa. The yield was 97.3%.

Comparative Example 2

Dimethyl 1,1-cyclolpropanedicarboxylate without polyethylene glycol/derivative addition 450.3 9 of 1,2-dichloroethane (4.55 mol) and 168 g of potassium carbonate (1.2 mol) were initially introduced and the reaction mixture was heated until the 1,2-dichloroethane refluxes. 99.1 g of dimethyl malonate (0.75 mol) and 1.25 g of tetrabutylammonium bromide (3.88 mmol) were then added at the boil. Water formed during the reaction was removed by azeotropic distillation with 1,2-dichloroethane throughout the reaction.

After a reaction time of 5 hours, the reaction mixture was cooled and separated off from the reaction salt by filtration. By means of fractional distillation, 1,2-dichloroethane was obtained at a reduced pressure and dimethyl 1,1-cyclopropanedicarboxylate was obtained at up to 10 mbar (=100 Pa). The yield was 79.7%.

Comparative Example 3

Preparation of dimethyl 1,1-cyclopropanedicarboxylate using a very good stirring element without polyethylene glycol/derivative addition The synthesis was carried out analogously to Comparative Example 2, the reaction mixture was stirred for 6 hours using a finely dispersing stirrer (Ultra Turrax). The yield was 90.8%.

EXAMPLE 1

Dimethyl 1,1-cyclopropanedicarboxylate 450.3 g of 1,2-dichloroethane (4.55 mol), 15.5 g of polyethylene glycol dimethyl ether (mean molar mass 250 g/mol) and 168.0 g of potassium carbonate (1.2 mol) were initially introduced, and the reaction mixture was heated until the 1,2-dichloroethane refluxes. 118.9 g of dimethyl malonate (0.9 mol) and 1.25 g of tetrabutylammonium bromide (3.88 mmol) were then added at the boil. The mixture was stirred using a finely dispersing stirrer (Ultra Turrax) for 6 hours. Water formed during the reaction was removed by azeotropic distillation with 1,2-dichloroethane throughout the reaction. Further work-up was carried out analogously to Comparative Example 2. The yield was 96.3%.

EXAMPLE 2

Dimethyl 1,1-cyclopropanedicarboxylate 296.9 g of 1,2-dichloroethane (3 mol), 15 g of polyethylene glycol dimethyl ether (mean molar mass 500 g/mol) and 177.1 g of potassium carbonate (1.265 mol) were initially introduced, and the reaction mixture was heated until the 1,2-dichloroethane refluxes. 125.5 g of dimethyl malonate (0.95 mol) and 1.25 g of tetrabutylammonium bromide (3.88 mmol) were then added at the boil. The mixture was stirred using a paddle stirrer for 6 hours. Water formed during the reaction was removed by azeotropic distillation with 1,2-dichloroethane throughout the reaction. Further work-up was carried out analogously to Comparative Example 2. The yield was 95%.

EXAMPLE 3

Dimethyl 1,1-cyclopropanedicarboxylate 296.9 g of 1,2-dichloroethane (3 mol), 5 g of polyethylene glycol monomethyl ether (mean molar mass 550 g/mol) and 177.1 g of potassium carbonate (1.265 mol) were initially introduced, and the reaction mixture was heated until the 1,2-dichloroethane refluxes. 125.5 g of dimethyl malonate (0.95 mol) and 1.25 g of tetrabutylammonium bromide (3.88 mmol) were then added at the boil. The mixture was stirred using a paddle stirrer for 6.5 hours. Water formed during the reaction was removed by azeotropic distillation with 1,2-dichloroethane throughout the reaction. Further work-up was carried out analogously to Comparative Example 2. The yield was 95%.

EXAMPLE 4

Dimethyl 1,1-cyclopropanedicarboxylate 319.6 g of 1,2-dichloroethane (3.23 mol), 5 g of polyethylene glycol (mean molar mass 600 g/mol) and 168.0 g of potassium carbonate (1.2 mol) were initially introduced, and the reaction mixture was heated until the 1,2-dichloroethane refluxes. 132.1 g of dimethyl malonate (1 mol) and 1.25 g of tetrabutylammonium bromide (3.88 mmol) were then added at the boil. The mixture was stirred using a paddle stirrer for 6 hours. Water formed during the reaction was removed by azeotropic distillation with 1,2-dichloroethane throughout the reaction. Further work-up was carried out analogously to Comparative Example 2. The yield was 87%.

EXAMPLE 5

Diethyl 1,1-cyclopropanedicarboxylate 296.9 g of 1,2-dichloroethane (3 mol), 5 g of polyethylene glycol monomethyl ether (mean molar mass 550 g/mol) and 177.1 g of potassium carbonate (1.265 mol) were initially introduced, and the reaction mixture was heated until the 1,2-dichloroethane refluxes. 152.2 g of diethyl malonate (0.95 mol) and 1.25 g of tetrabutylammonium bromide (3.88 mmol) were then added at the boil. The mixture was stirred using a paddle stirrer for 8 hours. Water formed during the reaction was removed by azeotropic distillation with 1,2-dichloroethane throughout the reaction. Further work-up was carried out analogously to Comparative Example 2. The yield was 85%.

Table 1 below shows the stoichiometric ratios of Comparative Examples 1 to 3 and of the Examples 1 to 5 according to the invention.

TABLE 1

Composition of Examples and Comparative Examples

| Substance | Comp. 1 | Comp. 2 | Comp. 3 | Ex.1 | Ex. 2 | Ex. 3 | Ex.4 | Ex.5 |
|---|---|---|---|---|---|---|---|---|
| | molar amount | | | | | | | |
| DMM | 1 | 1 | 1 | 1 | 1 | 1 | 1 | — |
| DEM | — | — | — | — | — | — | — | 1 |
| $K_2CO_3$ | 2.5 | 1.6 | 1.6 | 1.33 | 1.33 | 1.33 | 1.20 | 1.33 |
| EDC | 8.38 | 6.07 | 6.07 | 5.06 | 3.16 | 3.16 | 3.23 | 3.16 |
| TBAB | 0.3 | 0.0052 | 0.0052 | 0.0043 | 0.0041 | 0.0041 | 0.0039 | 0.0041 |
| | amount [g] | | | | | | | |
| PEG/DME 250 | — | — | — | 15.5 | — | — | — | — |
| PEG/DME 500 | — | — | — | — | 15 | — | — | — |
| PEG-M 500 | — | — | — | — | — | 5 | — | 5 |
| PEG 600 | — | — | — | — | — | — | 5 | — |
| Reaction time [h] | 7 | 5 | 6 | 6 | 6 | 6 | 6.5 | 8 |
| Yield [%] | 97.3 | 79.7 | 90.8 | 96.3 | 95 | 95 | 87 | 85 |

Abbreviations in Table 1:
DMM = dimethyl malonate, molar mass 132.12 g/mol
DEM = diethyl malonate, molar mass 160.17 g/mol
$K_2CO_3$ = potassium carbonate (potash), molar mass 139.97 g/mol
EDC = 1,2-dichloroethane, molar mess 98.96 g/mol
TBAB = tetrabutylammonium bromide, molar mass 322.37 g/mol
PEG-DME 250 = polyethylene glycol dimethyl ether, mean molar mass 250 g/mol
PEG-DME 500 = polyethylene glycol dimethyl ether, mean molar mass 500 g/mol
PEG-M 550 = polyethylene glycol monomethyl ether, mean molar mass 550 g/mol
PEG 600 = polyethylene glycol, mean molar mass 600 g/mol In the case of azeotropic removal of the water formed during the reaction, without addition of polyethylene glycol derivatives, an alkali metal carbonate (potassium carbonate) excess of 60% must be used in order to achieve a yield of 79.7% over the course of 5 hours with 0.52 mol % of alkylammonium halide (tetrabutylammonium bromide).

The use of a good agitating and dispersing stirring element (here Ultra-Turrax stirrer) serves to increase the yield to 90.8% under otherwise virtually identical conditions as in Comparative Example 3.

Example 1 shows that the addition of polyethylene glycol dimethyl ether (13.0% by weight, based on malonic diester) produces a yield of >96% over the course of 6 hours for a 33% potassium carbonate excess.

Example 3 shows that the addition of polyethylene glycol monomethyl ether (4% by weight, based on malonic diester) leads to a yield of 95% over the course of 6.5 hours for a 33% potassium carbonate excess.

The addition of polyethylene glycol (3.8% by weight, based on malonic diester) in Example 4 produces a yield of 87% over the course of 6 hours for a 20% potassium carbonate excess under otherwise virtually identical reaction conditions as in Example 3. The priority document of the present application, German patent application 199 63 115.8-44, filed Dec. 24, 1999, is incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed is:
1. A process for the preparation of 1,1-cyclopropanedicarboxylic diesters, comprising:

a) reacting in a solvent-free environment malonic diester, 1,2- dihaloethane and alkali metal carbonate in the presence of available or in-situ-produced phase transfer catalyst and polyalkylene glycol or at least one derivative of polyalkylene glycol which is capped at one or both ends;

wherein a molar ratio of malonic diester: 1,2-dihaloethane: alkali metal carbonate is 1:(1 to 7):(1 to 1,4);

wherein a reaction temperature is $\geq 70°$ C.;

b) azeotropically distilling off water produced during the reaction with 1,2-dihaloethane;

c) separating off the reaction salt by a mechanical separation operation;

d) distilling off an excess of 1,2-dihaloethane; and e) fractionally distiling off said 1,1-cyclopropanedicarboxylic diester;

wherein said reacting proceeds according to the schematic reaction equation

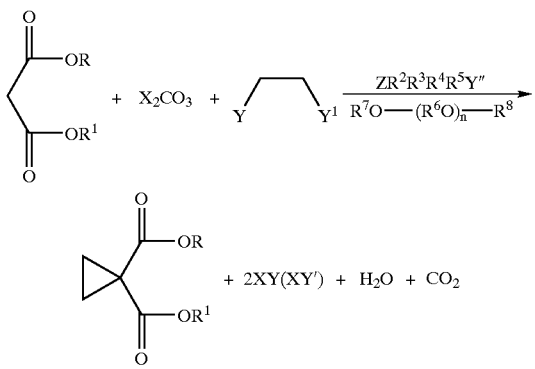

wherein R and $R^1$ independently are an unbranched or branched alkyl group having from 1 to 6 carbon atoms;

Z is nitrogen or phosphorus; and $R^2, R^3, R^4$ and $R^5$ independently are an unbranched or branched alkyl group having from 1 to 16 carbon atoms, an aryl, alkylaryl or arylalkyl radical having from 6 to 12 carbon atoms or a 1,2dihaloethyl group;

n is an integer or a fraction from 1 to 30;

$R^6$ is an ethylene radical, a propylene radical, or a mixed compound with ethylene and propylene radicals, and $R^7$ and $R^8$ independently are a hydrogen radical, an unbranched or branched alkyl group having from 1 to 6 carbon atoms or an acyl group having from 2 to 7 carbon atoms;

Y and Y' independently are chlorine, bromine or iodine;

Y" is chloride, bromide, iodide or hydrogen sulfate; and

X is Na or K.

2. The process according to claim 1, wherein the molar ratio of malonic diester: 1,2-dihaloethane: alkali metal carbonate is 1:(2.5 to 3.8):(1.1 to 1.4).

3. The process according to claim 1, wherein said malonic diester is dimethyl malonate, diethyl malonate, methylethyl malonate or a mixture thereof.

4. The process according to claim 1, wherein said 1,2-dihaloethane is 1,2-dichloroethane.

5. The process according to claim 1, wherein said 1,2-dihaloethane has different halogen atoms selected from chloride, bromide and iodide.

6. The process according to claim 1, wherein said alkali metal carbonate is sodium carbonate, potassium carbonate or a mixture thereof.

7. The process according to claim 6, wherein said potassium carbonate has a fines content of 85% <0.1 mm and 70% <0.05 mm.

8. The process according to claim 1, wherein said phase transfer catalyst is a quaternary ammonium salt, a quaternary phosphonium salt or a mixture thereof.

9. The process according to claim 1, wherein said phase transfer catalyst is a tetraalkylammonium salt selected from the group consisting of a tetrabutylammoniumhalide, a benzyltrimethyl ammonium salt, a tetrabutylphosphonium salt or a mixture thereof.

10. The process according to claim 1, wherein said phase transfer catalyst is a quaternary alkylammonium halide.

11. The process according to claim 10, wherein said phase transfer catalyst is tetrabutylammonium bromide.

12. The process according to claim 1, wherein said polyalkylene glycol is polyethylene glycol.

13. The process according to claim 1, wherein said derivative of said polyalkylene glycol is capped at one or both ends by a methyl or an ethyl group.

14. The process according to claim 13, wherein said polyethylene glycol is capped at one or both ends by an ether group.

15. The process according to claim 1, wherein a concentration of said polyalkylene glycol or said derivative of polyalkylene glycol is from 1 to 20% based on said malonic diester.

16. The process according to claim 1, wherein a content of said phase transfer catalyst is <0.5 mol % based on said malonic ester.

17. The process according to claim 1, wherein said polyalkylene glycol or said derivative of polyalkylene glycol has a mean molar mass of from 100 to 800 g/mol.

18. The process according to claim 1, wherein an amount of said dihaloethane is <3.2 mol based on 1 mol of said malonic ester.

19. The process according to claim 1, wherein said malonic diester, said 1,2-dihaloethane, said alkali metal carbonate, said phase transfer catalyst, said polyalkylene glycol or said derivative of polyalkylene glycol are introduced initially and the mixture is heated to boiling temperature.

20. The process according to claim 1, wherein the phase transfer catalyst is metered in at the boil.

21. The process according to claim 1, wherein the malonic diester is metered in at the boil.

22. The process according to claim 1, wherein said phase transfer catalyst is produced in situ.

23. The process according to claim 1, wherein n is an integer from 2 to 20.

24. The process according to claim 22, wherein said please transfer catalyst is produced in situ from trialkylamine and 1,2-dihaloethane.

25. The process according to claim 1, wherein said phase transfer catalyst and said malonic diester are metered in together at the boil.

26. The process according to claim 1, wherein said molar ratio of malonic diester: 1,2-dihaloethane: alkali carbonate is 1:(3.16–5.06): 1.33.

27. The process according to claim 1, wherein said molar ratio of malonic diester: 1,2,-dihaloethane: alkali carbonate is 1:3.16:1.33.

28. The process according to claim 1, wherein said molar ratio of malonic diester: 1,2-dihaloethane: alkali is 1:3.23:1.20.

29. The process according to claim 1, wherein said molar ratio of malonic diester: 1,2-dihaloethane: alkali carbonate is 1:5.06:1.33.

30. A process for the preparation of 1,1-cylopropane dicarboxylic diesters, comprising:

a) reacting in an environment consisting of malonic diester, 1,2-dihaloethane and alkali metal carbonate in the presence of available or in-situ-produced phase transfer catalyst and polyalkylene glycol or at least one derivative of polyalkylene glycol which is capped at one or both ends;

wherein a molar ration of malonic diester: 1,2-dihaloethane: alkali metal carbonate is 1:(1 to 7):(1 to 1,4);

wherein a reaction temperature is $\geq 70°$ C.;

b) azeotropically distilling off water produced during the reaction with 1,2-dihaloethane;

c) separating off the reaction salt by a mechanical separation operation;

d) distilling off an excess of 1,2-dihaloethane; and e) fractionally distilling off said 1,1-cyclopropanedicarboxylic diester;

wherein said reacting proceeds according to the schematic reaction equation

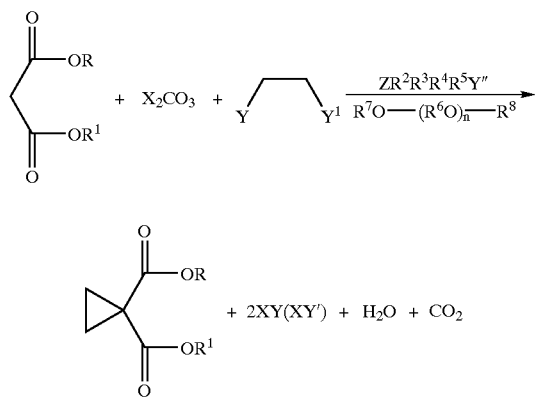

wherein R and $R^1$ independently are an unbranched or branched alkyl group having from 1 to 6 carbon atoms;

Z is nitrogen or phosphorus; and $R^2$, $R^3$, $R^4$ and $R^5$ independently are an unbranched or branched alkyl group having from 1 to 16 carbon atoms, an aryl, alkylaryl or arylalkyl radical having from 6 to 12 carbon atom or a 1,2-dihaloethyl group;

n is an integer or a fraction from 1 to 30;

$R^6$ is an ethylene radical, a propylene radical, or a mixed compound with ethylene and propylene radicals, and $R^7$ and $R^8$ independently are a hydrogen radical, an unbranched or branched alkyl group having from 1 to 6 carbon atoms or an acyl group having from 2 to 7 carbon atoms;

Y and Y' independently are chlorine, bromine or iodine;

Y" is chloride, bromide, iodide or hydrogen sulfate; and

X is Na or K.

* * * * *